United States Patent
Camilleri et al.

(10) Patent No.: US 6,835,712 B1
(45) Date of Patent: Dec. 28, 2004

(54) COMPOUNDS (75) Inventors: Patrick Camilleri, Harlow (GB); Philippe Guedat, Lyons (FR); Anthony John Kirby, Cambridge (GB); Andreas Kremer, Harlow (GB)

(73) Assignees: SmithKline Beecham p.l.c., Brentford (GB); Cambridge University Technical Services Ltd. (GB)

( * ) Notice: Subject to any disclaimer, the term of this patent is extended or adjusted under 35 U.S.C. 154(b) by 76 days.

(21) Appl. No.: 10/018,547

(22) PCT Filed: Jun. 16, 2000

(86) PCT No.: PCT/GB00/02364

§ 371 (c)(1),
(2), (4) Date: Jul. 19, 2002

(87) PCT Pub. No.: WO00/77032

PCT Pub. Date: Dec. 21, 2000

(30) Foreign Application Priority Data

Jun. 16, 1999 (GB) .............................. 9914045

(51) Int. Cl.⁷ ............................ A61K 38/00; C07K 7/02
(52) U.S. Cl. .......................... 514/2; 530/328; 424/78.27
(58) Field of Search ............................ 514/2; 530/328; 424/78.27

(56) References Cited

U.S. PATENT DOCUMENTS 5,744,335 A    4/1998 Fritz et al.
6,693,167 B1 *  2/2004 Camilleri et al. ........... 530/328

FOREIGN PATENT DOCUMENTS

| AU | WO00/27795 A | 5/2000 |
| GB | WO99/29712 A | 6/1999 |
| WO | WO/9703939 A | 2/1997 |
| WO | WO/9718185 A | 5/1997 |
| WO | WO/9840502 A | 6/1998 |

OTHER PUBLICATIONS

Ekrami, H., Kennedy, AR, Witschi H, Shen, WC. "Cationized Bowman–Birk protease inhibitor as a targeted cancer chemopreventive agent." J Drug Target 1993; 1(1):41–49.*
R.S. Weeks, et al. "Novel Lysine–spermine Conjugate Alters In Vivo And In Vitro Tumor Cell Growth Through Inhibition Of Polyamine Transport" *Proceedings of The 1999 AACR–NCI–Eortc International Conference On Molecular Targets and Cacer Therapeutics*, vol. 5(Abs.189): (Nov., 1999).
G Byk, et al., "Synthesis, Activity and Structure–Activity Relationship Studies Of Novel Cationic Lipids For DNA Transfer". *Journal of Medicinal Chemistry, US, American Chemical Society, Washington*, vol. 41 (2): 224–235 (Jan. 15, 1998).

* cited by examiner

*Primary Examiner*—Karen Cochrane Carlson
*Assistant Examiner*—Anand U Desai
(74) *Attorney, Agent, or Firm*—William R. Majarian; Stephen Venetianer; Charles M. Kinzig (57) ABSTRACT

Spermine:peptide-based surfactant compounds are disclosed. The compounds are based on a spermine backbone with peptide groups and optionally hydrocarbyl groups linked thereto. Uses of the spermine:peptide-based surfactant compounds and methods for their production are also disclosed.

20 Claims, 5 Drawing Sheets

COMPOUNDS

CROSS REFERENCES TO RELATED APPLICATIONS

This application is a National Stage Application filed under 35 U.S.C.§371 of PCT/GB00/02364, filed on Jun. 16, 2000.

This invention relates to newly identified spermine:peptide-based surfactant compounds, to the use of such compounds and to processes for their preparation. The invention also relates to the use of the spermine:peptide-based surfactant compounds to facilitate the transfer of compounds into cells for drug delivery.

Surfactants are substances that markedly affect the surface properties of a liquid, even at low concentrations. For example surfactants will significantly reduce surface tension when dissolved in water or aqueous solutions and will reduce interfacial tension between two liquids or a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega, Y et al., Kolloidn. Zh. 36, 649, 1974). These molecules, which have been termed "gemini" (Menger, F M and Littau, C A, J.Am.Chem.Soc. 113, 1451, 1991), have very desirable properties over their monomeric equivalents. For example they are highly effective in reducing interfacial tension between oil and water based liquids and have a very low critical micelle concentration.

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. WI, USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao,X et al. (1995) Gene Ther. 2, 710–722 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., Nature Medicine, 1, 39–46, 1995). More recently other groups have investigated the potential of other cationic lipids for gene delivery, for example cholesterol derivatives (Oudrhiri,N et al. Proc.Natl.Acad.Sci. 94, 1651–1656, 1997). This limited study demonstrated the ability of these cholesterol based compounds to facilitate the transfer of genes into epithelial cells both in vitro and in vivo, thereby lending support to the validity of this general approach.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. The present invention seeks to overcome the difficulties exhibited by existing compounds.

The invention relates to spermine:peptide-based surfactant compounds having a spermine backbone and having the general structure of formula (I):

where $R_1$ and $R_3$ are hydrogen and $R_2$ and $R_4$, which may be the same or different, are peptide groups formed from one or more amino acids linked together, in a linear or branched manner, by amide (CONH) bonds and further linked to the spermine backbone by amide bonds, having the general formula (II):

where p1 is 0 to 5 and p2 is 1 to 5, preferably 1; and the values for p3 and p4, which may be the same or different, are from 0 to 5, preferably 0;

A1, A3 and A4, which may be the same or different, are amino acids selected from serine, lysine, ornithine, threonine, histidine, cysteine, arginine and tyrosine; and A2 is an amino acid selected from lysine, ornithine and histidine;

and $R_5$ and $R_6$ are saturated or unsaturated hydrocarbyl groups having up to 24 carbon atoms and linked to the spermine backbone by an amide or an amine ($NCH_2$) linkage;

or where $R_1$ and $R_3$ are hydrogen, $R_2$ and $R_4$, which may be the same or different are saturated or unsaturated hydrocarbyl groups having up to 24 carbon atoms and linked to the spermine backbone by amide or amine bonds, and $R_5$ and $R_6$, which may be the same or different, are peptide groups of formula (II) linked to the spermine backbone by amide bonds;

or a salt, preferably a pharmaceutically acceptable salt thereof.

When used herein, the term "hydrocarbyl" refers to a group having from 1 to 24 carbon atoms which may be in a straight chain or a branched chain and include a saturated carbocyclic ring having from 3 to 6 carbon atoms and which chain may contain unsaturation (double and/or triple carbon-carbon bonds).

The amide linkages between the amino acids A1, A2 and A3 in the peptide group of formula (II) are standard peptide bonds (α bonds), unless the amino acid is a diamine, for example lysine or ornithine, where the linkage may involve either of the two amine groups. For example, where A1 is lysine, the linkage to the amino acid A2 may be a standard alpha amide bond, or an epsilon (ε) amide bond involving the amine of the lysine side chain. Similarly where A1 is ornithine the amide bond linking A1 to A2 may be an alpha bond or a delta (δ) bond that is created using the amine on the side chain of the ornithine amino acid residue.

Preferably, the compound is symmetrical, that is $R_1$ and $R_3$ are the same, $R_2$ and $R_4$ are the same, and $R_5$ and $R_6$ are the same. Symmetrical spermine:peptide-based surfactant compounds of the invention are "gemini" surfactants.

In a preferred embodiment A1 in the group of formula (II) is serine or threonine, prefereably serine. Preferably A3 and A4 in the group of formula (II) are lysine, ornithine, histidine or arginine.

In a further preferred embodiment the hydrocarbyl group is selected from:
—$CO(CH_2)_{10}CH_3$
—$CO(CH_2)_{12}CH_3$
—$CO(CH_2)_{14}CH_3$
—$CO(CH_2)_{16}CH_3$
—$CO(CH_2)_{18}CH_3$
—$CO(CH_2)_{22}CH_3$
—$CO(CH_2)_7CH=CH(CH_2)_5CH_3$
—$CO(CH_2)_7CH=CH(CH_2)_7CH_3$
—$CO(CH_2)_7CH=CHCH_2CH=CH(CH_2)_4CH_3$
—$CO(CH_2)_7(CH=CHCH_2)_3CH_3$
—$CO(CH_2)_3CH=CH(CH_2CH=CH)_3(CH_2)_4CH_3$
—$CO(CH_2)_7CH=CH(CH_2)_5CH_3$ Trans
—$CO(CH_2)_7CH=CH(CH_2)_7CH_3$ Trans
—$CO(CH_2)_8CHCH_3(CH_2)_7CH_3$
—$COCHOH(CH_2)_{21}CH_3$ In another preferred embodiment the hydrocarbyl group is selected from:
—$(CH_2)_{11}CH_3$
—$(CH_2)_{13}CH_3$
—$(CH_2)_{15}CH_3$
—$(CH_2)_{17}CH_3$
—$(CH_2)_{19}CH_3$
—$(CH_2)_{23}CH_3$
—$(CH_2)_8CH=CH(CH_2)_5CH_3$
—$(CH_2)_8CH=CH(CH_2)_7CH_3$
—$(CH_2)_8CH=CHCH_2CH=CH(CH_2)_4CH_3$
—$(CH_2)_8(CH=CHCH_2)_3CH_3$
—$(CH_2)_4CH=CH(CH_2CH=CH)_3(CH_2)_4CH_3$
—$(CH_2)_8CH=CH(CH_2)_5CH_3$ Trans
—$(CH_2)_8CH=CH(CH_2)_7CH_3$ Trans
—$(CH_2)_9CHCH_3(CH_2)_7CH_3$ Compounds of the present invention may be prepared from readily available starting materials using synthetic peptide chemistry well known to the skilled person. The scheme shown in FIGS. 1a and 1b shows a general process for the synthesis of the compounds of the invention wherein the hydrocarbyl groups are linked to the spermine moiety by amine bonds and the scheme shown in FIGS. 2a and 2b shows a general process for the synthesis of the compounds of the invention wherein the carbonyl groups are linked to the spermine moiety by amide bonds.

Figure 1A:
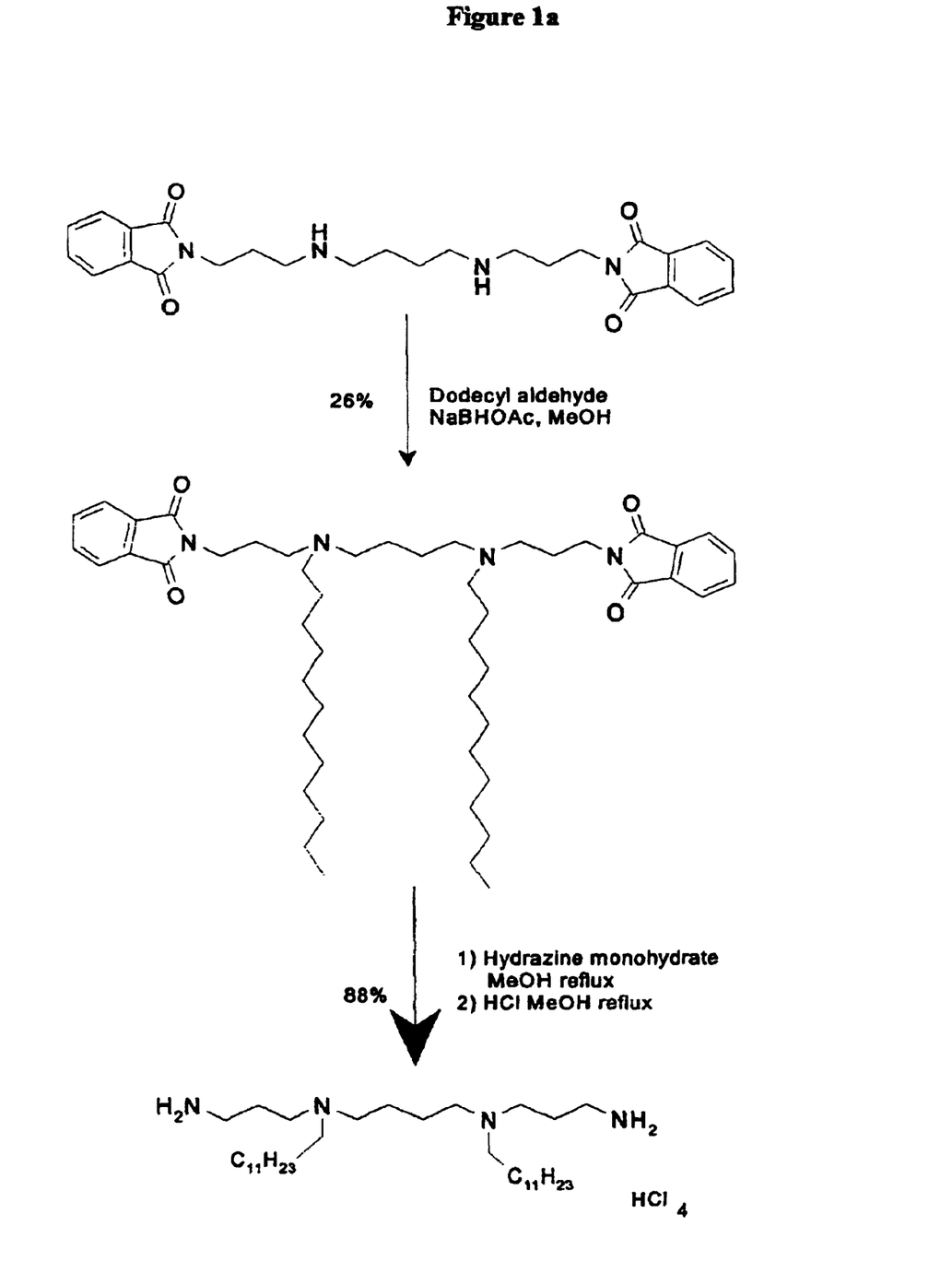
FIG. 1a and FIG. 1b. General scheme for synthesis of spermine:peptide-based surfactant compounds wherein the carbonyl groups (in this instance dodecanoyl) are linked to the spermine moiety by amine bonds. The final compound in FIG. 1a is the first compound in FIG. 1b.
Figure 1B:
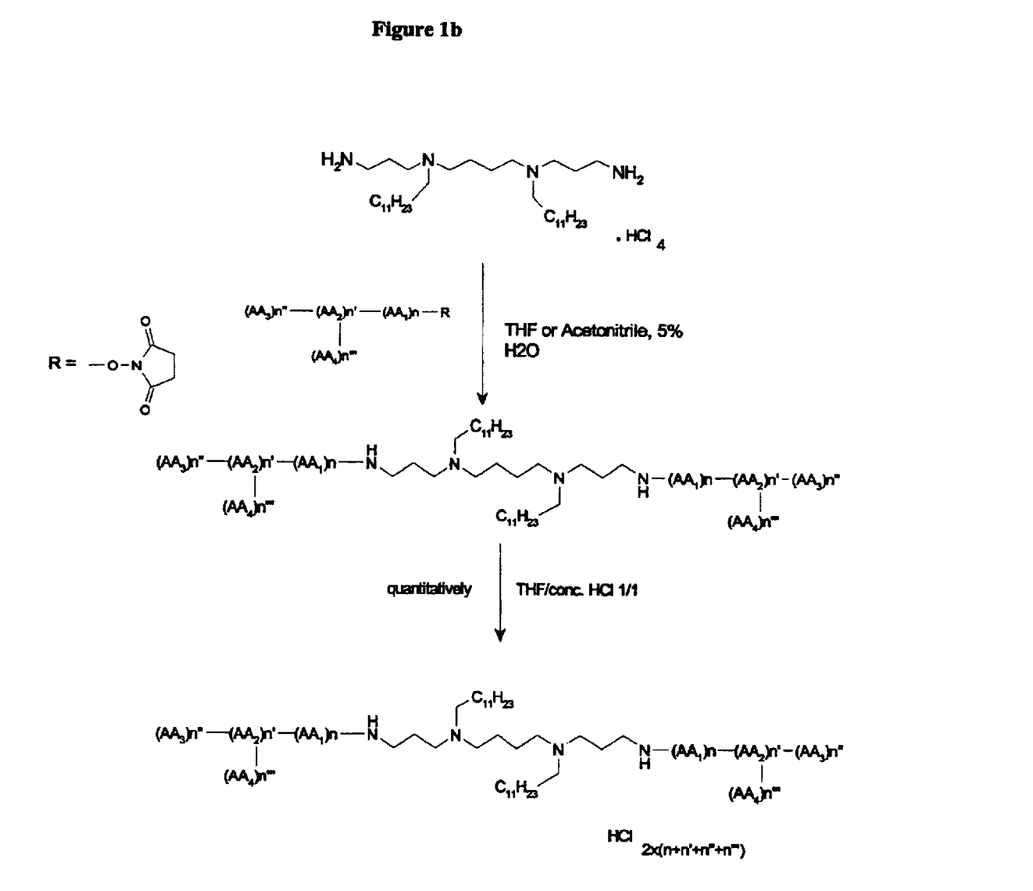
Figure 2A:
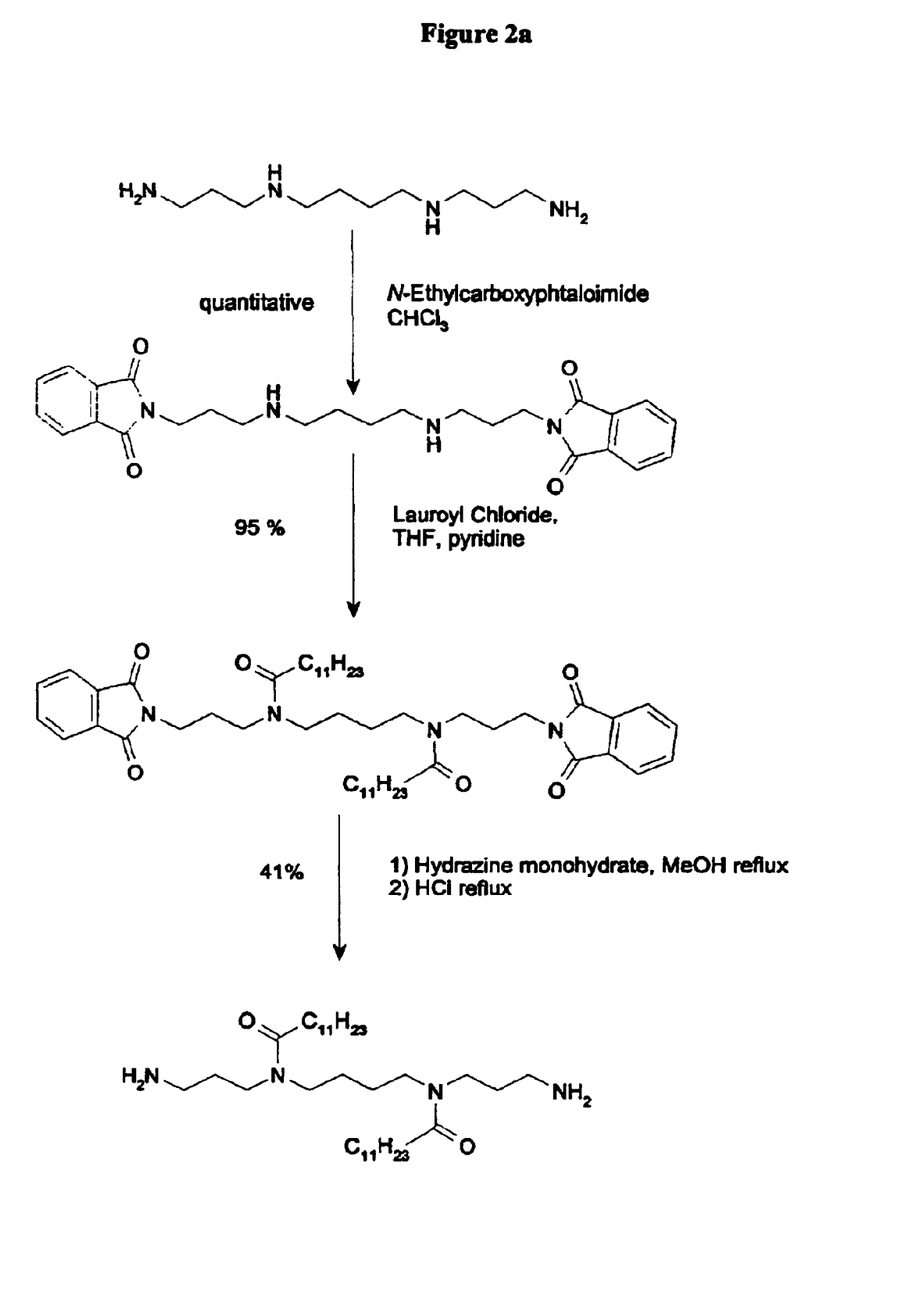
FIG. 2a and FIG. 2b. General scheme for synthesis of spermine:peptide-based surfactant compounds wherein the carbonyl groups (in this instance dodecanoyl) are linked to the spermine moiety by amide bonds. The final compound in FIG. 2a is the first compound in FIG. 2b.
Figure 2B:
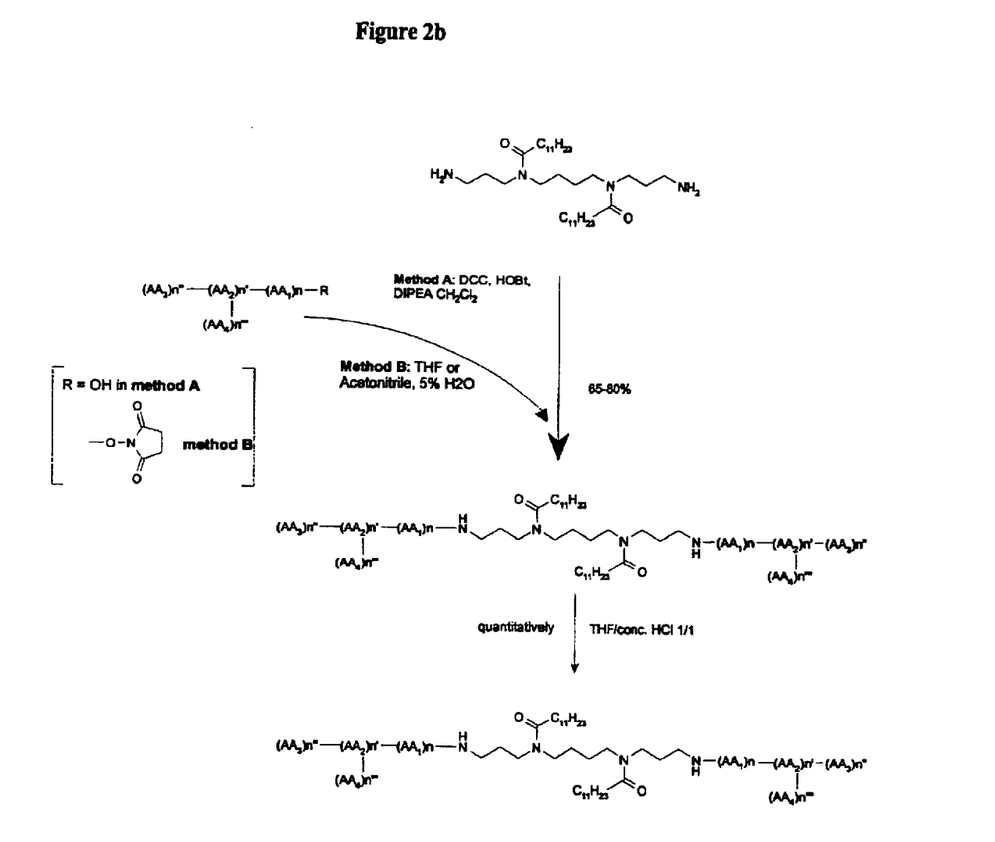
Figure 3:
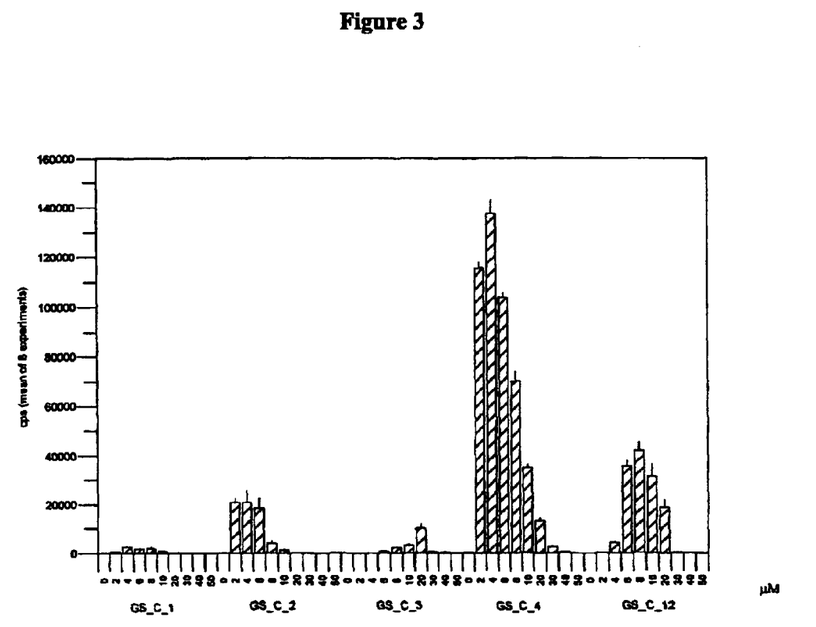
FIG. 3. Transfection of CHO-K1 cells (stable transfected with beta-galactosidase) with spermine:peptide-based gemini surfactants GS-C-1, GS-C-2, GS-C-3, GS-C-4, and GS-C-12. Bars represent the mean cps (counts per second) of 8 experiments ± the standard error of the mean.

The processes shown in FIGS. 1 and 2 are for the synthesis of symmetrical, that is "gemini", spermine:peptide-based surfactants. Non-symmetrical spermine:peptide-based surfactants of the invention can be prepared by introducing asymmetry, for example at the primary amines of spermine, by using different protecting groups. Suitable nitrogen protecting groups are well known in the art and are described in, for example, "Protective Groups in Organic Chemistry" (T. W. Greene, Wiley-Interscience, New York, 2nd Edition, 1991).

Another aspect of the invention relates to methods for using the spermine:peptide-based surfactant compounds. Such uses include facilitating the transfer of DNA or RNA polynucleotides, or analogs thereof, into a eukaryotic or prokaryotic cell in vivo or in vitro. These uses include facilitating transfection of polynucleotides to achieve an antisense knock-out effect, for gene therapy and genetic immunization (for the generation of antibodies) in whole organisms. Other uses include employing the compounds of the invention to facilitate the transfection of polynucleotides into cells in culture when such transfer is required, in, for example, gene expression studies and antisense control experiments among others. The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqmar® method (Perkin Elmer, Connecticut, USA). Compounds of the invention offer a significant improvement, typically between 3 and 6 fold, in the efficiency of cellular uptake of DNA in cells in culture, compared with compounds in the previous art. In the transfection protocol, the gemini compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta* 1235 289);

(ii) a complexing reagent, for example the commercially available PLUS reagent (Invitrogen, Maryland, USA) or peptides, such as polylysine or polyornithine peptides or peptides comprising primarily, but not exclusively, basic amino acids such as lysine, ornithine and/or arginine. The list above is not intended to be exhaustive and other supplements that increase the efficiency of transfection are taken to fall within the scope of the invention.

In still another aspect, the invention relates to the transfer of genetic material in gene therapy using the compounds of the invention.

Yet another aspect of the invention relates to methods to effect the delivery of non-nucleotide based drug compounds into cells in vitro and in vivo using the compounds of the invention.

In a further aspect, the invention relates to methods to facilitate the transfer of a polynucleotide or an anti-infective compounds into prokaryotic or eukaryotic organism for use in anti-infective therapy.

The following definitions are provided to facilitate understanding of certain terms used frequently herein.

"Amino acid" refers to dipolar ions (zwitterions) of the form $^+H_3NCH(R)CO_2^-$. They are differentiated by the nature of the group R, and when R is different from hydrogen can also be asymmetric, forming D and L families. Amino acids may be natural or un-natural amino acids. There are 20 naturally occurring amino acids where the R group can be, for example, non-polar (e.g. alanine, leucine, phenylalanine) or polar (e.g. glutamic acid, histidine, arginine and lysine). In the case of un-natural amino acids R can be any other group which is not found in the amino acids found in nature.

"Polynucleotide" generally refers to any polyribonucleotide or polydeoxyribonucleotide, which may be unmodified RNA or DNA or modified RNA or DNA. "Polynucleotides" include, without limitation single-and double-stranded DNA, DNA that is a mixture of single-and double-stranded regions, single-and double-stranded RNA, and RNA that is mixture of single-and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL*, 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

The invention will now be described by way of the following examples.

EXAMPLES

Example 1

Synthesis of GSC1

Step 1:

A solution of N-carbethoxyphthalimide (4 mmol, 439 mg) in chloroform (5 ml) was added as one portion at room temperature to a stirred solution of spermine (2 mmol, 406.7 mg) in chloroform (5 ml). The mixture was stirred for 1 hour and the solvent was removed, the crude was dried under good vacuum to get the title compound without further purification (Sosnovsky, G. (1986) Zeitschrift für Naturforschung 41b:122–129).

Step 2:

The protected spermine 350 mg (0.76 mmol) was dissolved in 10 ml of dry THF, the Lauroyl chloride 3 eq (2.28 mmol) and 2 ml of dry pyridine was added. After refluxing 30 min, the mixture was stirred at room temperature overnight. Solvent was removed, and the crude was dissolved in AcOEt (25 ml) and was washed with saturated bicarbonate (2×20 ml). The organic phase was dried over anhydrous sodium sulfate and evaporated. The resulting oil was chromatographied on silica gel with AcOEt/hexane (1:1 to 4:1) rf=0.20 (AcOEt/hexane 1:1) to yield 490 mg (84%) of bis-dodecyl as oil which crystallized as white semi-solid crystal. $^1$H-NMR (CDCl$_3$): 7.9–7.6 m (8H (—C$_6$H$_4$—)$_2$); 3.7–3.6 m (4H); 3.4–3.2 m (8H); 2.3–2.1 m (4H); 2.0–1.8 m (4H); 1.6–1.4 m (8H); 1.3–1.1 m (32H); 0.9–0.8 m (6H). $^{13}$C-NMR (CDCl$_3$): 173.1, 173.0, 172.9, 172.8, 168.3, 168.2, 134.2, 134.1, 133.9, 133.8, 132.2, 132.1, 132.0, 131.9, 123.4, 123.2, 47.6, 45.7, 45.5, 45.4, 43.5, 43.4, 35.9, 33.9, 33.2, 33.1, 30.9, 29.6, 29.5, 29.4, 29.3, 29.1, 28.3, 28.2, 27.1, 26.7, 26.4, 25.5, 25.4, 25.2, 25.1, 24.9, 22.7, 14.1

Step 3:

The bis-phthalimide (400 mg, 0.48 mmol) was dissolved in 20 ml of MeOH, hydrazine monohydrate 0.4 ml was added and the mixture was refluxed 6 H. Solvent was removed, and the crude redissolved in MeOH (20 ml) and 2 ml of concentrated HCl was added. The mixture was refluxed for 30 min, and solvent was removed. The residue was dissolved in aqueous NaOH 10%, the precipitate was filtrated and wash with 3 amount of cold water. The residue was dried to give 112 mg (41%) of white powder. $^1$H-NMR (MeOH): 3.21 t ($^3$J=6.8 Hz, 4H); 2.6–2.5 m (8H); 2.76 t ($^3$J=7.5 Hz, 4H); 1.7–1.5 m (12H); 1.4–1.2 m (32H); 0.89 t ($^3$J=6.9 Hz, 6H (—CH$_3$)$_2$).

Step 4:

The diamine 100 mg (0.176 mmol), HOBt 2 eq (0.353 mmol, 54 mg), BOC$_2$Lys 2.4 eq (0.423 mmol, 135 mg) and DIPEA 2 eq (0.353 mmol, 62 ml) was dissolved in CH$_2$Cl$_2$ (20 ml). The mixture was cooled at −10° C. and DCC 2.4 eq (0.423 mmol, 87 mg) was added. The mixture was stirred at −10° C. and allowed to reach room temperature very slowly and set aside overnight. The DCU was removed by filtration, and solvent was evaporated off. The crude was redissolved in AcOEt (30 ml), was washed successively 4% NaHCO$_3$ (2×15 ml), 4% citric acid (2×15 ml), water (20 ml) and finally brine (20 ml). Organic phase was dried over anhydrous sodium sulfate and was evaporated to dryness. The residue was chromatographied on silica gel and was eluated with hexane/AcOEt 1/1 (rf=0.01) to AcOEt/MeOH 9/1 (rf= 0.6) yield 152 mg (71%) as oil. $^1$H-NMR (CDCl$_3$): 7.05 sbroad(1H); 6.69 sbroad (1H); 5.6–4.7 m (6H); 4.9–4.1 m (4H); 3.7–3.0 m (16H); 2.2–2.0 m (6H); 2.0–1.0 m (88H); 0.88 t ($^3$J=6.8 Hz, 6H (—CH$_3$)$_2$).

Step 5:

The tetra-protected Gemini 150 mg (0.12 mmol) was dissolved in CH$_2$Cl$_2$/TFA 1/1 (25 ml) and was stirred at room temperature for 0.5 H. Solvent was removed to give the deprotected compounds as a TFA salt which was exchanged on anionic Dowex 1×8 to get the tetrahydrochloride salt as a sticky oil. The compound was redissolved in small amount of MeOH and precipitate with ether, solvent was removed by decantation, this was repeated three times, to give GSC1. $^1$H-NMR (MeOH): 3.8–3.1 m (8H); 3.0–2.8 m (4H); 2.2–2.1 m (4H); 2.0–1.4 m (26H); 1.4–1.2 m (36H); 0.90 t ($^3$J=6.8 Hz, 6H (—CH$_3$)$_2$). M/z (H$^+$): 823.75; (2H$^+$): 412.38.

Example 2

Synthesis of GSC4

Step 1:

The diamine 150 mg (0.265 mmol) was dissolved in 5% aqueous acetonitrile (10 ml) and triethylamine 2.2 eq (0.6 mmol, 80 µl) was added. The Nα,Nε-bis-ter-butyl-carbamate-L-lysine-L-serine-O-succinimidate (was built by the usual peptide synthesis) 2 eq (0.528 mmol, 280 mg) in acetonitrile (8 ml) was added slowly. The mixture was stirred 48 H at room temperature, and solvent was removed. The crude was redissolved in AcOEt (30 ml), was washed successively water (2×20 ml), 3% HCl (2×20 ml), water (20 ml) and finally brine (20 ml). Organic phase was dried over anhydrous sodium sulfate and was evaporated to dryness, to yield 252 mg (68%). $^1$H-NMR (CDCl$_3$): 4.9–4.1 m (4H); 3.6–3.0 m (20H); 2.2–2.0 m (8H); 2.0–1.0 m (80H); 0.88 t ($^3$J=6.8 Hz, 6H (—CH$_3$)$_2$).

Step 2:

The tetra-protected Gemini 248 mg (0.177 mmol) was dissolved in THF/HClconc 1/1 (25 ml) and was stirred at room temperature for 1 H. Solvent was removed to give the deprotected compounds as a sticky dark oil which was redissolved in small amount of MeOH and precipitate with ether, solvent was removed by decantation, this was repeated several times, to yield 120 mg (60%) GSC4 as pink powder. $^1$H-NMR (MeOH): 4.0–3.9 m (2H); 3.5–3.2 m; 3.1–2.9 m (4H); 2.5–2.3 m (4H); 2.3–2.1 m (1H); 2.0–1.5 m (20H); 1.4–1.2 m (32H); 0.90 t ($^3$J=6.8 Hz, 6H (—CH$_3$)$_2$).

Example 3

Synthesis of GSC40

Step 1:

The diamine 120 mg (0.212 mmol), HOBt 2.5 eq. (0.53 mmol, 72 mg), (BOC$_2$Lys)Lys 2.5 eq. (0.53 mmol, 426 mg) and DIPEA 2.5 eq. (0.53 mmol, 92 µl) was dissolved in CH$_2$Cl$_2$/THF 1/1 (20 ml). The mixture was cooled at −10° C. and DCC 2.4 eq. (0.508 mmol, 105 mg) was added. The mixture was stirred at −10° C. and allowed to reach room temperature very slowly and set aside overnight. The DCU was removed by filtration, and the solvent was evaporated off. The crude product was redissolved in EtOAc (30 ml), was washed successively with 4% NaHCO$_3$ (2×15 ml), 4% citric acid (2×15 ml), water (20 ml) and finally brine (20 ml). the organic phase was dried over anhydrous sodium sulfate and was evaporated to dryness. The residue was chromatographed on silica gel and was eluated with hexane/EtOAc 1/1 (rf=0.01) to EtOAc/MeOH 9/1 (rf=0.55) yield 210 mg (46%) as oil. $^1$H-NMR (CDCl$_3$): 4.9–4.6 m (2H); 4.1–3.9 m (4H); 3.5–2.9 m (16H); 2.3–2.1 m (2H); m (164H); 0.88 t ($^3$J=6.8 Hz, 6H (—CH$_3$)2).

Step 2:

The octa-protected gemini 200 mg (0.094 mmol) was dissolved in THF/HClconc 1/1 (20 ml) and was stirred at room temperature for 1 H. The solvent was removed to give the deprotected compounds as a yellow oil which was redissolved in small amount of MeOH and precipitate with ether, the solvent was removed by decantation, this was repeated several times, to yield 130 mg (85%) GSC40 as yellow powder.

Example 4

Synthesis of GSC41

Step 1:

The diamine 200 mg (0.35 mmol) was dissolved in 5% aqueous acetonitrile (20 ml) and triethylamine 2 eq. (0.7 mmol, 0.1 ml) was added. The bis-(Nα,Nε-bis-ter-butyl-carbamate-L-lysine)-L-lysine-L-serine-O-succinimidate 2 eq (0.71 mmol, 700 mg) in acetonitrile (10 ml) was added slowly. The mixture was stirred 48 H at room temperature, and solvent was removed. The crude product was redissolved in AcOEt (30 ml), was washed successively water (2×20 ml), 3% HCl (2×20 ml), water (20 ml) and finally brine (20 ml). The organic phase was dried over anhydrous sodium sulfate and was evaporated to dryness, to yield 509 mg (63%). $^1$H-NMR (CDCl$_3$): 4.9–4.6 m; 4.1–3.9 m (4H); 3.6–2.9 m (22H); 2.3–2.1 m (4H); 2.0–1.0 m; 0.88 t ($^3$J=6.8 Hz, 6H (—CH$_3$)2).

Step 2:

The tetra-protected gemini 499 mg (0.216 mmol) was dissolved in THF/HClconc 1/1 (30 ml) and was stirred at room temperature for 1 H. the solvent was removed to give the deprotected compounds as a sticky brawn oil which was redissolved in small amount of MeOH and precipitated with ether, solvent was removed by decantation, this was several times, to yield 350 mg (90%) GSC41 as brown powder.

Example 5

Synthesis of GSC42

Step 1:

The diamine 200 mg (0.35 mmol) was dissolved in 5% aqueous acetonitrile (20 ml) and triethylamine 2 eq. (0.7 mmol, 0.1 ml) was added. The bis-(Nα,Nε-bis-ter-butyl-carbamate-L-lysine)-L-lysine-L-serine-O-succinimidate 2 eq (0.71 mmol, 700 mg) in acetonitrile (10 ml) was added slowly. The mixture was stirred 48 H at room temperature, and solvent was removed. The crude product was redissolved in AcOEt (30 ml), was washed successively water (2×20 ml), 3% HCl (2×20 ml), water (20 ml) and finally brine (20 ml). The organic phase was dried over anhydrous sodium sulfate and evaporated to dryness, to yield 522 mg (70%). $^1$H-NMR (CDCl$_3$): 6.7–6.6 m (2H); 5.5–5.3 m (2H); 4.9–4.6 m (4H); 4.5–4.3 m (4H); 4.1–3.9 m (4H); 3.5–2.9 m (20H); 2.3–2.1 m (4H); 1.9–1.0 m; 0.88 t ($^3$J=6.8 Hz, 6H (—CH$_3$)2).

Step 2:

The tetra-protected Gemini 517 mg (0.242 mmol) was dissolved in THF/HClconc 1/1 (30 ml) and was stirred at room temperature for 1 H. The solvent was removed to give the deprotected compounds as a sticky dark oil which was redissolved in small amount of MeOH and precipitate with ether, solvent was removed by decantation, this was repeated several times, to yield 346 mg (88%) GSC42 as brown powder.

Example 6

Synthesis of GSC2

Step 1:

The protected spermine 1.23 g (2.65 mmol) was dissolved in 1,2-dichloroethane (25 ml) and dodecyl aldehyde 2.5 eq. (6.6 mmol, 1.5 ml) was added. After 10 mn, the sodium cyanoborohydride 6 eq. (15.9 mmol, 1 g) was added and the mixture was stirred at room temperature overnight. Then sodium cyanoborohydide 4.5 eq. (750 mg) was added again and mixture was stirred overnight at room temperature. This solution was partitioned between dichloromethane (150 ml) and water (150 ml) and the pH was adjusted to 9. The resulting emulsion was left in a separating funnel for 12 H. Then, the organic phase was dried over sodium sulfate and concentrated. The crude product was chromatographed on silica gel, eluated with EtOAc/Hexane 1/4 to 1/2 (rf: 0.3) containing 0.1% of NEt$_3$, to yield 540 mg of semi-solid yellow compound (26%).

Step 2:

The protected spermine 200 mg (0.25 mmol) was dissolved in methanol (10 ml) and hydrazine monohydrate 10 eq (2.5 mmol, 0.13 ml) was added. The mixture was refluxed for 8 H, and the solvent was removed. The crude product was redissolved in 10 ml of methanol and conc. HCl (2 ml) was added, the mixture was refluxed for 30 min, cooled in ice and filtered. The solvent was removed and the crude product redissolved in dichloromethane (30 ml), stirred 30 min at room temperature and the precipate was removed by filtration. The solution was evaporated and dried under reduce pressure to yield 150 mg GSC2 as a yellow semi-solid compound (88%).

Example 7

Synthesis of GSC12

Step 1:

The diamine 143 mg (0.265 mmol) was dissolved in 5% aq. THF (10 ml) and NEt$_3$ 0.6 mmol (80 ml), activated peptide 2 eq (0.528 mmol, 282 mg) in THF (5 ml) were added. The mixture was stirred overnight and concentrated. Then, the crude product was dissolved in EtOAc (60 ml) and was washed successively with water (2×20 ml) 3% HCl (2×20 ml) water (20 ml) brine (20 ml). The organic phase was dried over sodium sulfate and the solvent was evaporated to yield 210 mg of a sticky white compound (58%).

Step 2:

The tetra-Boc 200 mg (0.146 mmol) was dissolved in THF/conc. HCl 1/1 (20 ml) and was stirred at room temperature for 1 H. The solvent was removed and the crude product was redissolved in small amount of MeOH and precipitated with ether, cooled to −20° C., the solvent was removed by decantation, this was repeated several times, to yield 150 mg (87%) GSC12 as a yellow powder.

Example 8

Transfection of Recombinant Plasmid Expressing Luciferase into Cells Using Spermine:Peptide-Based Surfactant Compounds Transfection studies were performed using the adherent cell line CHO-K1 (Puck et al. 1958). Complete medium consisted of MEM alpha medium supplemented with 10% v/v foetal bovine serum and 1× L-Glutamine. All media and supplements were obtained from Invitrogen.

Stable transfected cell lines expressing β-galactosidase were generated by cotransfection of the plasmid pSV-β-Galactosidase Control Vector (Promega) with the plasmid Selecta Vecta-Neo (R & D Systems) in a 10:1 ratio. Following G418 (Invitrogen) selection (0.8 mg ml$^{-1}$), candidate cell lines were tested for β-galactosidase activity (β-Gal Reporter Gene Assay, chemiluminescent; Roche Diagnostics).

In Vitro Gene Transfection

Cells were seeded into 96-well MTP plates (Beckton Dickinson) 16–18 hours prior to transfection at an approximate density of 1×10$^4$ cells per well. For transfection, 64 ng of the luciferase reporter gene plasmid, pGL3-Control Vector (Promega) per well, was incubated with various concentrations of the spermine:peptide-based surfactant compounds and complexing agents. After 30 minutes incubation at RT, OPTI-MEM® medium (Invitrogen) was added to the transfection mixture and the solution placed on the cells (final volume per well: 100 μl). Following a 3 hour or over night incubation at 37° C., the transfection solution was replaced with complete medium and the cells incubated further at 37° C. Reporter gene assays were performed according to the manufacturer's guidelines (Roche Diagnostics) approximately 48 hours post transfection. Luminescence was measured in a Packard TopCount NXT Microplate Scintillation and Luminescence Counter. For normalization purpose, β-galactosidase activity (β-Gal Reporter Gene Assay, chemiluminescent; Roche Diagnostics) was measured and luciferase activity per β-galactosidase activity was calculated.

What is claimed is:

1. A spermine:peptide-based surfactant compound having the general structure of formula (I):

wherein $R_1$ and $R_3$ are hydrogen and $R_2$ and $R_4$, which may be the same or different, are peptide groups formed from one or more amino acids linked together, in a linear or branched manner, by amine (CONH) bonds and further linked to the spermine backbone by amide bonds, having the general formula (II):

wherein p1 is 0 to 5 and p2 is 1 to 5; and the values for p3 and p4, which may be the same or different, are from 0 to 5; A1, A3 and A4, which may be the same or different, are amino acids selected from the group consisting of serine, lysine, ornithine, threonine, histidine, cysteine, arginine and tyrosine; and A2 is an amino acid selected from the group consisting of lysine, ornithine and histidine;

and $R_5$ and $R_6$ are saturated or unsaturated hydrocarbyl groups having up to 24 carbon atoms and linked to the spermine backbone by an amide or an amine ($NCH_2$) linkage;

or where $R_1$ and $R_3$ are hydrogen, $R_2$ and $R_4$, which may be the same or different are saturated or unsaturated hydrocarbyl groups having up to 24 carbon atoms and linked to the spermine backbone by amide or amine bonds, and $R_5$ and $R_6$, which may be the same or different, are peptide groups of formula (II) linked to the spermine backbone by amide bonds;

and pharmaceutically acceptable salts thereof.

2. A spermine:peptide-based surfactant compound according to claim 1 which is symmetrical, that is $R_1$ and $R_3$ are the same, $R_2$ and $R_4$ are the same, and $R_5$ and $R_6$ are the same.

3. A spermine:peptide-based surfactant compound according to claim 1 wherein in the peptide group of formula (II) p1 is 1 and p2, p3 and p4 are all 0.

4. A spermine:peptide-based surfactant compound according to claim 1 wherein in the peptide group of formula (II) p1 and p2 are both 1 and p3 and p4 are both 0.

5. A spermine:peptide-based surfactant compound according to claim 1 wherein in the peptide group of formula (II) p1 is 0 and p2, p3 and p4 are all 1.

6. A spermine:peptide-based surfactant compound according to claim 1 wherein in the peptide group of formula (II) p1 and p2 are 0, p2 is 1 and p4 is 2.

7. A spermine:peptide-based surfactant compound according to claim 1 wherein the A1 is serine.

8. A spermine:peptide-based surfactant compound according to claim 1 wherein the A2 is lysine.

9. A spermine:peptide-based surfactant compound according to claim 1 wherein the hydrocarbyl group is selected from the group consisting of:

—$(CH_2)_{11}CH_3$;
—$(CH_2)_{13}CH_3$;
—$(CH_2)_{15}CH_3$;
—$(CH_2)_{17}CH_3$;
—$(CH_2)_{19}CH_3$;
—$(CH_2)_{23}CH_3$;
—$(CH_2)_8CH=CH(CH_2)_5CH_3$;
—$(CH_2)_8CH=CH(CH_2)_7CH_3$;
—$(CH_2)_8CH=CHCH_2CH=CH(CH_2)_4CH_3$;
—$(CH_2)_8(CH=CHCH_2)_3CH_3$;
—$(CH_2)_4CH=CH(CH_2CH=CH)_3(CH_2)_4CH_3$;
—$(CH_2)_8CH=CH(CH_2)_5CH_3$ Trans;
—$(CH_2)_8CH=CH(CH_2)_7CH_3$ Trans; and
—$(CH_2)_9CHCH_3(CH_2)_7CH_3$.

10. A spermine:peptide-based surfactant compound according to claim 1 wherein the hydrocarbyl group is selected from the group consisting of:

—$CO(CH_2)_{10}CH_3$;
—$CO(CH_2)_{12}CH_3$;
—$CO(CH_2)_{14}CH_3$;
—$CO(CH_2)_{16}CH_3$;
—$CO(CH_2)_{18}CH_3$;
—$CO(CH_2)_{22}CH_3$;
—$CO(CH_2)_7CH=CH(CH_2)_5CH_3$;
—$CO(CH_2)_7CH=CH(CH_2)_7CH_3$;
—$CO(CH_2)_7CH=CHCH_2CH=CH(CH_2)_4CH_3$;
—$CO(CH_2)_7(CH=CHCH_2)_3CH_3$;
—$CO(CH_2)_3CH=CH(CH_2CH=CH)_3(CH_2)_4CH_3$;
—$CO(CH_2)_7CH=CH(CH_2)_5CH_3$ Trans;
—$CO(CH_2)_7CH=CH(CH_2)_7CH_3$ Trans;
—$CO(CH_2)_8CHCH_3(CH_2)_7CH_3$;
—$COCHOH(CH_2)_{21}CH_3$;

$$-CO(CH_2)_9CH\underset{\underset{H_2}{C}}{\overset{\diagdown\;\diagup}{\hphantom{xx}}}CH(CH_2)_5CH_3; \text{ and}$$

$$\underset{\underset{CO(CH_2)_{12}CH_3}{|}}{COCH}-(CH_2)_{10}CH_3$$

11. The compound of claim 1 having the formula:

12. The compound of claim 1 having the formula:

13. The compound of claim 1 having the formula:

14. The compound of claim 1 having the formula:

15. The compound of claim 1 having the formula:

16. The compound of claim 1 having the formula:

17. The compound of claim 1 having the formula:

18. The compound of claim 1 having the formula:

19. A method of introducing DNA or RNA polynucleotides or analogs thereof into a eukaryotic or prokaryotic cell in vivo comprising contacting the cell with the compound of claim 1 and a DNA or RNA polynucleotide or analog thereof.

20. A process for preparing spermine:peptide-based surfactant compounds of claim 1 which process comprises forming an amide bond between a hydrocarbylated spermine backbone and a peptide comprising one or more amino acids.

* * * * *